United States Patent [19]

Mato, Jr.

[11] Patent Number: 4,751,460
[45] Date of Patent: Jun. 14, 1988

[54] METHOD AND APPARATUS FOR NONDESTRUCTIVE INSPECTION OF MAGNETIC PIPING

[75] Inventor: Stephan A. Mato, Jr., Katy, Tex.

[73] Assignee: Western Atlas International, Inc., Houston, Tex.

[21] Appl. No.: 869,635

[22] Filed: Jun. 2, 1986

[51] Int. Cl.$^4$ ............... G01N 27/87; G01N 27/90
[52] U.S. Cl. ................................................. 324/221
[58] Field of Search ...................... 324/219–221, 324/233, 234, 236–240, 243, 262; 340/856–859

[56] References Cited

U.S. PATENT DOCUMENTS

| | | | |
|---|---|---|---|
| 3,225,293 | 12/1965 | Wood et al. | 324/221 |
| 3,543,144 | 11/1970 | Walters et al. | 324/221 |
| 3,786,684 | 1/1974 | Wiers et al. | 324/220 X |
| 3,940,689 | 2/1976 | Johnson, Jr. | 324/221 |
| 3,967,194 | 6/1976 | Beaver et al. | 324/220 |

*Primary Examiner*—Reinhard J. Eisenzopf
*Assistant Examiner*—Warren S. Edmonds
*Attorney, Agent, or Firm*—Patrick H. McCollum

[57] ABSTRACT

Method and apparatus for nondestructive inspection of oilfield piping includes first and second pole pieces and a electromagnetic core therebetween for emitting a unidirectional magnetic flux field into the piping. A plurality of detector shoes each house a flux leakage coil assembly and a corresponding eddy current coil assembly. Circuits receive, process and transmit signals from the individual flux leakage coil assemblies to the surface. At the surface each signal is processed individually to provide indications of mass loss and/or gain as detected by each flux leakage coil assembly.

7 Claims, 3 Drawing Sheets

METHOD AND APPARATUS FOR NONDESTRUCTIVE INSPECTION OF MAGNETIC PIPING

BACKGROUND OF THE INVENTION

This invention relates to improved methods and apparatus for evaluating the condition of subsurface oilfield piping and, more particularly, relates to magnetic, induction type apparatus for nondestructive testing of tubing and casing.

It is common knowledge in the petroleum industry to use steel or iron pipe in nearly all oil and gas wells. Such piping serves useful purposes including shutting off water bearing formations, preventing formation deterioration and shutting off intermediate oil or gas zones when it is desired to drill deeper. During the lifetime of a well a variety of conditions may result in the deterioration of such subsurface piping, including pits, cracks, holes, thin walls, structure changes in the metal and the like. Such deterioration may result from various causes. Electrochemical theory postulates a tendency of steel, or other materials, in an electrolytes environment, such as subsurface formations, to go into solution causing corrosive deterioration. Likewise, during drilling operations drill pipe collars may rub on the inside wall of the pipe causing excessive wear.

There have been various proposals for the design of equipment to measure pipe anomalies while the piping is still in place. One such system which has been widely accepted by the industry is described in U.S. Pat. No. 3,543,144, issued to W. T. Walters et al on Nov. 24, 1970. This system includes an elongated magnetizer assembly including a pair of elongated pole pieces, having a diameter only slightly less than the inside diameter of the piping, and a central core having a magnetizing winding thereon between the pole pieces. A plurality of detectors are positioned between the pole pieces into contact with the interior surface of the casing. A high-intensity, undirectional magnetic field emits from the magnetizing winding with the object of saturating the ferrous piping. If there is no defect in the piping, the magnetic flux lines pass undisturbed through the piping between the pole pieces. When a defect in the casing exists a portion of the magnetic field will "leak" out the piping and flow about the defect. This flow is detected within the wall contact detectors.

For detection of magnetic flux lines, each shoe includes two coils which detect flux leakage. In addition, each shoe includes two coils to detect eddy current flow. When a flux leakage coil detects flux leakage the companion eddy current coil generates a signal if the defect is inside the casing wall. Electrical signals of the greatest signal from the shoes in the upper ring and the greatest the signal from the shoes of the lower ring are generated and transmitted to the surface. A third recording indicates whether the defect is internal. Lastly, all signals from the upper ring are processed to yield an average measurement of the circumferential extent of the defect.

While the system described has found acceptance in nondestructive testing of subsurface piping it has proven less than desirable in indicating the nature of anomalous response obtained. All tool responses must be treated as corrosive unless prior knowledge of the well indicates otherwise. Thus, to interpret subsurface signals an operator is required to employ actual records of the well indicating the presence of equipment such as centralizers and scratchers. Otherwise all signal responses are treated as a defect. This leads to problems, particularly if well records are incomplete or inaccurate.

These and other disadvantages are overcome with the present invention by providing an apparatus for nondestructive testing of well casings which does not require prior knowledge of the well and provides a plurality of quantative indications of casing condition.

SUMMARY OF THE INVENTION

The present invention provides method and apparatus for the nondestructive inspection of oilfield piping. The method and apparatus utilize a cylindrical core member disposed between two elongated nonmagnetic housing members. Two groups of detector shoes are supported between a pair of arm carriers also serving as pole pieces. A magnetic coil is wound on the core between the arm carriers. A undirectional magnetic field emitted by the coil assemblies permeates the casing wall with magnetic lines of flux. Detector shoes detect changes in the magnetic lines of flux caused by defects in the piping. Each detector shoe includes a coil assembly for detecting flux leakage and a coil assembly for detecting eddy currents. The flux leakage signal from each flux leakage coil assembly is amplified, filtered and used to amplitude modulated a carrier signal for transmission to the surface. At the surface each flux leakage signal is filtered, demodulated, recorded and processed to provide a plurality of direct indications of mass loss and/or gain.

DETAILED DESCRIPTION OF A PREFERRED EMBODIMENT

Figure 1:
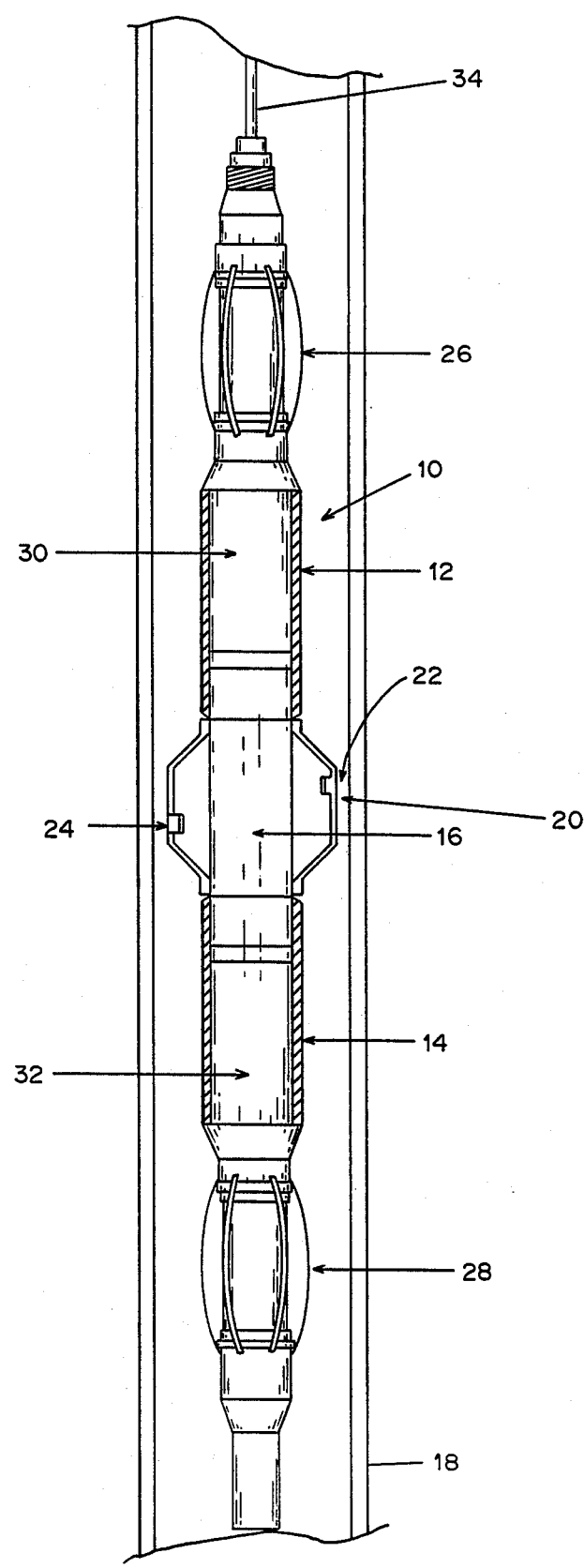
FIG. 1 is a pictorial view, partly in cross-section, of a casing inspection instrument disposed in a section of casing.

Referring now to FIG. 1, there is illustrated a magnetic induction type corrosion inspection instrument 10. Instrument 10 includes upper and lower magnetic pole pieces, 12 and 14 respectfully, which are elongated cylindrical members for coupling magnetic flux into adjacent well casing 18. Magnetic core 16, a core of a soft iron material wound with layers of wire to form an electromagnetic, generates a undirectional magnetic flux field when DC current is passed through the winding. The magnetic flux flows through a closed loop including core 16, pole pieces 12 and 14, and the casing located between pole pieces 12 and 14. Sensors 20 are placed around core 16 and biased into contact with the inner wall of casing 18. Sensors 20 are positioned in two parallel rings, upper ring 22 and lower ring 24, to form a staggered, overlapping array to produce full 360 degree scanning of the casing. Centralizers 26 and 28 maintain instrument 10 centered along the longitudinal axis of casing 18. Subsurface electronic packages 30 and 32 are enclosed within pole pieces 12 and 14, respectfully. Instrument 10 is suspended by wireline or cable 34 which contains electrical conductors for supplying electrical power to instrument 10 and transmitting electrical signals form instrument 10 to the surface. A more detailed description of the mechanical configuration of instrument 10 can be found in U.S. Pat. No. 3,543,144, issued Nov. 24, 1970 to W. T. Walters et al, which is incorporated herein by reference.

Figure 2:
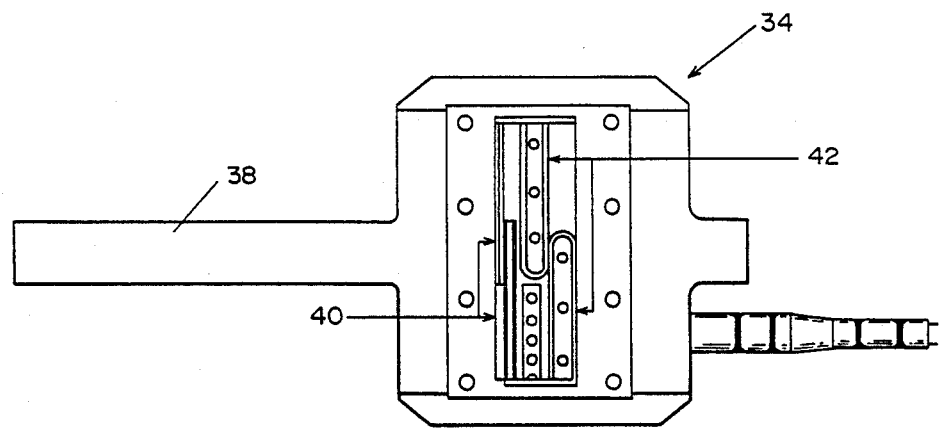
FIG. 2 is a pictorial view of a detector shoe illustrating the FL and EC sensor coils.

Referring now to FIG. 2, there is illustrated a detector shoe 34 of the type comprising sensors 20. Detector shoe 34 includes a detect housing section 36 and an elongated outrigger 38. Mounted within housing section 36 are two sets of sensors, flux leakage, FL, 40 and eddy current, EC, 42. FL sensors 40 are oriented with a coil axis parallel to the longitudinal axis of the casing and function to determine the depth and extent of defects. EC sensors 42 are oriented with a coil axis perpendicular to the casing axis and function to determine whether defect are external or internal.

Figure 3:
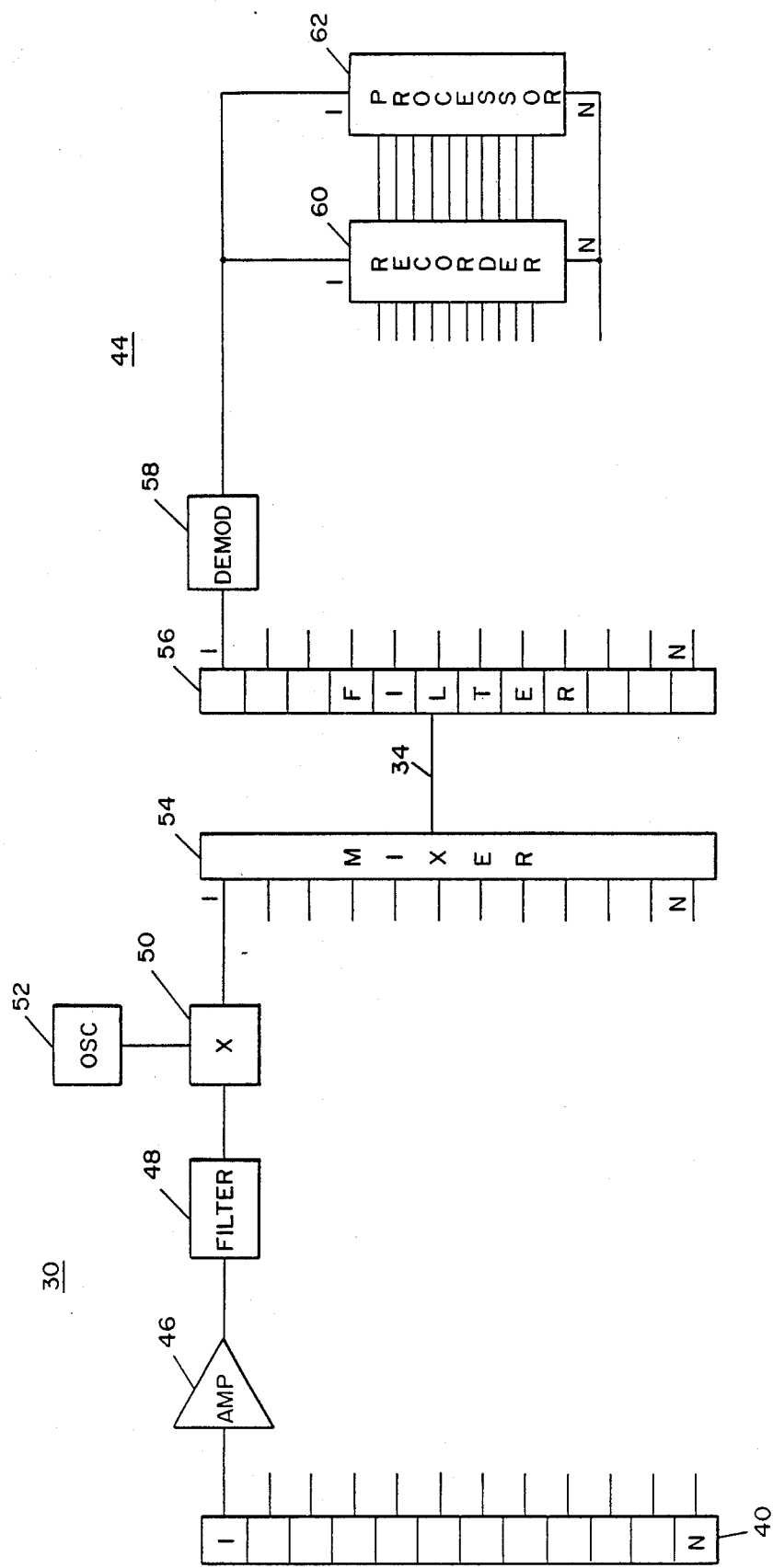
FIG. 3 is a sample block diagram of the subsurface and surface electronics for processing FL signals.

Referring to FIG. 3, there is illustrated a portion of subsurface electronics 30 and surface electronics 44 used for processing FL sensor signals. As previously described FL sensors 1-N, 40, are housed within housing section 36 of detector shoes 34. The number of sensors 20 will vary depending on the size of instrument 10 which is dictated by the internal diameter of casing 18. In the illustrated embodiment twelve FL sensors 40 are shown. Although processing currently is illustrated for only one FL sensor it should be recognized that identical circuits are used for each additional FL sensor, 2-N.

The output of FL sensor FL-1 is coupled into amplifier circuit 46 where it is amplified. The output of amplifier 46 is coupled into low-pass filter 48 where undesirable noise is removed. The output of filter 48 is coupled into multiplier circuit 50. A second input of multiplier circuit 50 is coupled to the output of oscillator circuit 52. Multiplier circuit 50 serves as a precision multiplier the output of which is an amplitude modulated signal. It should be recognized that each oscillator for FL channels 1-N is set to a unique value. In the preferred embodiment the frequency of each oscillator is as follows: FL1, 2 kHz; FL2, 2.5 kHz; FL3, 3.0; FL4, 4.0; FL5, 4.5; FL6, 5.0; FL7, 6 kHz; FL8, 7 kHz; FL10, 9 kHz; FL11, 11 kHz; FLN, 14 kHz. The amplitude modulated signal from multiplier 50 is coupled to one input of mixer 54. Mixer 54 combines Fl sensor signals, FL-1-N, for transmission over an electrical conductor in wireline 34 to the surface electronics 44.

At the surface the FL sensor signals, FL-1-N, are coupled into band pass filters 56, one filter for each FL channel. The output of filter 56 is coupled into demodulator 58 the output of which is an electrical signal representative of the output of the respective subsurface FL sensor. The output of demodulator 58 is coupled into the input of recorder 60 and processor 62. Recorder 60 can be any suitable type recording device common in well logging, for example, a magnetic tape unit, a plotter, or a camera. Processor 62 can take the form of any suitable digital computer, for example a Perkin-Elmer 8/16 E, or specially designed processing circuitry.

In the operating of the casing inspection apparatus illustrated in FIGS. 1-3, instrument 10 is caused to traverse casing 18 by winding cable 34 onto and from a drum (not shown) located at the surface. As instrument 10 traverses casing 18 a DC electromagnetic field permeates the casing wall with magnetic lines of flux. If there is no defect in the casing, the flux lines pass from one of the instrument's poles, through the casing, and back to the other pole. If there is a defect in the casing, the electromagnetic field will be altered. To detect such altered fields, instrument 10 includes two sets of contact shoes, upper and lower rings 22 and 24. Each shoe includes flux leakage, FL, sensors 40 and eddy current, EC, sensors 42.

While the typical prior art casing inspection instrument processed only two FL signals, the largest from each ring of sensors, the present invention contemplates using FL signals from all FL sensors. Each respective FL signal is amplified, filtered and is used to amplitude modulate a carrier signal, the frequency of which is unique for each FL sensor, before being mixed for transmission to the surface. At the surface each FL sensor signal is filtered, demodulated to recover the FL signal, recorded and processed.

Figure 4:
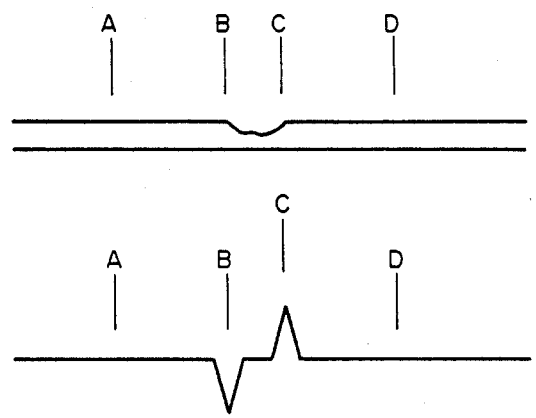
FIG. 4 illustrates the FL sensor signal response to a pit within casing.

Referring now to FIG. 4, there is illustrated in simplified form an FL signal response to a pit within the casing. If the casing wall is constant, section A, the FL sensor signal will be relatively constant. When the FL sensor passes the first edge of the pit, B, the body wall of the casing is reduced (mass loss). This mass loss causes a change in the level of the magnetic field at the FL sensor, causing a signal output proportional to the change and in a predetermined direction indicating a mass loss. When the sensor passes the other edge of the pit, C, the wall effectively increases in relation to the pit section (mass gain). The increase in mass relative to the pit causes a signal change in the positive direction, indicating a mass gain. Once the sensor passes the pit area it is again in casing with a constant body, section D, hence no signal change is indicated. Thus, it can be established that a signal resulting from added mass is opposite in polarity to a signal caused by loss of mass, that the amplitude of the signal is proportional to the degree of corrosion and the width is proportional to the width of the pit.

Similar results are derived from the presence of casing collars and completion equipment, such as scratchers and centralizers. These devices will initially cause a signal indication of mass gain when the device is detected followed by an indication of mass loss when the device is passed.

Yet another example relates to presence of surface casing. An instrument 10 approaches the second string of casing (the surface casing), the effective wall suddenly appears thicker, due to the presence of the lower end of the surface casing about the outside of the production string. If the two casing strings are concentric the signals on all FL channels will be equal and indicate a mass gain, a signal reaction in only one direction, with no corresponding indication of mass loss. However, since casings are rarely concentric, being more typically eccentric, or in contact the signals from the FL channels will be unequal and indicate the relative offset position of the lower end of the surface casing in relation to the production string.

It is difficult to interpret corrosion underneath or just inside the casing shoe. A complex magnetic field pattern occurs here with the casing shoe response generally much larger that the corrosion. The closer the surface string is to touching the inner string, the more difficult the interpretation. The detector shoe that detects the corrosion experiences an influence of both mass loss and mass gain, so the signal is bipolar. The ratio of the gained mass amplitude to the loss mass amplitude yields an estimate of the depth of penetration of the pitting.

It is therefore apparent that the present invention is one well adapted to obtain all of the advantages and features hereinabove set forth, together with other advantages which will become obvious and apparent from a description of the apparatus itself. It will be understood that certain combinations and subcombinations are of utility and may be employed without reference to other features and subcombinations. Moreover, the foregoing disclosure and description of the invention are only illustrative and explanatory thereof, and the invention admits of various changes in size, shape and material composition of its components, as well as in the details of the illustrated construction, without departing from the scope and spirit thereof.

The embodiments of the invention in which an exclusive property or privilege is claimed are defined as follows:

1. A system for the nondestructive testing of piping, including an inspection instrument connected by an electrical cable to signal processing circuitry, comprising:

first and second magnetic pole pieces;
an electromagnet for emitting a magnetic flux field into the piping, said electromagnet located between said first and second pole pieces;
a plurality of detector shoes biased into contact with the interior surface of said piping for sensing said flux field;
circuit means coupled to each of said plurality of detector shoes for generating a corresponding plurality of electrical signals and sending all of said plurality of electrical signals through said electrical cable to said signal processing circuitry, each of said plurality of signals indicative of changes in mass of said piping proximate each of said plurality of detector shoes, respectively;
wherein said circuit means for each of said plurality of detector shoes further comprises:
an oscillator for providing a signal at a preselected frequency;
a multiplier circuit having one input coupled to said oscillator and a second input coupled to said detector shoe, the output of said multiplier circuit being an electrical signal corresponding to said oscillator signal amplitude modulated with said detector shoe signal; and
means for combining said multiplier circuit output signal for each of said plurality of detector shoes.

2. The apparatus of claim 1 wherein said circuit means for each of said plurality of detector shoes further comprises:
band pass filter means for generating an electrical signal output in response to said preselected frequency of said oscillator; and
demodulate means for generating an electrical signal output corresponding to said signal from said detector shoe.

3. The apparatus of claim 2 further comprising recorder means for recording said demodulator means electrical signal output as an indicator of the character of said piping proximate each of said plurality of detector shoes.

4. Apparatus for the nondestructive testing of piping, comprising:
first and second elongated magnetic pole pieces;
an electromagnet for emitting a unidirectional magnetic flux field into said piping, said electromagnet located between said first and second pole pieces;
a plurality of detector shoes contacting the interior surface of said piping for sensing said flux field, said detector shoes each including a flux leakage detector coil assembly, each of said flux leakage detector coil assemblies generating an electrical signal in response to said flux field;
circuit means for combining said plurality of electrical signals into a composite electrical signal representatives of the total circumferential changes in mass of said piping;
wherein said circuit means further comprise:
a plurality of oscillator circuits, each having a unique frequency signal output therefore;
a plurality of multiplier circuits for combining said electrical signal from each of said detector coil assemblies with a signal from each of said oscillators and generating a plurality of output electrical signals therefore; and
mixer means for combining said plurality of multiplier output signals into a composite electrical signal.

5. The apparatus of claim 4 wherein said circuit means further comprises:
band pass filter means for separating said composite electrical signal into a plurality of electrical signals directly related to the output of said plurality of multiplier circuits; and
demodulator means for separating said signal from said band pass filter means into a plurality of electrical signals directly related to the output of said flux leakage detector coils.

6. The apparatus of claim 5 wherein said detector shoes further comprise a plurality of detector shoes arranged to detect said flux field over approximately the full circumference of said piping.

7. The apparatus of claim 6 wherein the flux leakage detector coil axis is parallel to the longitudinal axis of said piping.

* * * * *